US00PP21589P2

(12) United States Plant Patent
Wood

(10) Patent No.: US PP21,589 P2
(45) Date of Patent: Dec. 28, 2010

(54) ***CLETHRA* PLANT NAMED 'CALEB'**

(50) Latin Name: *Clethra alnifolia*
Varietal Denomination: Caleb

(75) Inventor: Timothy D. Wood, Spring Lake, MI (US)

(73) Assignee: Spring Meadow Nursery, Inc., Grand Haven, MI (US)

( * ) Notice: Subject to any disclaimer, the term of this patent is extended or adjusted under 35 U.S.C. 154(b) by 0 days.

(21) Appl. No.: 12/462,539

(22) Filed: Aug. 5, 2009

(51) Int. Cl.
*A01H 5/00* (2006.01)

(52) U.S. Cl. ..... Plt./226

(58) Field of Classification Search ..... Plt./226
See application file for complete search history.

*Primary Examiner*—June Hwu
(74) *Attorney, Agent, or Firm*—C. A. Whealy

(57) ABSTRACT

A new and distinct cultivar of *Clethra* plant named 'Caleb', characterized by its upright and somewhat outwardly spreading plant habit; vigorous growth habit; freely branching habit; dark-green leaves; large inflorescences with numerous large flowers; and good garden performance.

2 Drawing Sheets

Botanical designation: *Clethra alnifolia.*
Cultivar denomination: 'Caleb'.

BACKGROUND OF THE INVENTION

The present invention relates to a new and distinct cultivar of *Clethra* plant, botanically known as *Clethra alnifolia* and hereinafter referred to by the name 'Caleb'.

The new *Clethra* plant is a product of a planned breeding program conducted by the Inventor in Grand Haven, Mich. The objective of the breeding program is to develop new *Clethra* cultivars with large inflorescences flowers.

The new *Clethra* plant originated from an open-pollination in August, 2003 of *Clethra alnifolia* 'Ruby Spice', not patented, as the female, or seed, parent with an unknown selection of *Clethra alnifolia*, as the male, or pollen, parent. The new *Clethra* plant was discovered and selected by the Inventor in August, 2005 as a single flowering plant within the progeny of the stated open-pollination in a controlled environment in Grand Haven, Mich.

Asexual reproduction of the new *Clethra* plant by softwood cuttings in a controlled greenhouse environment in Grand Haven, Mich. since the spring of 2006 has shown that the unique features of this new *Clethra* plant are stable and reproduced true to type in successive generations of asexual reproduction.

SUMMARY OF THE INVENTION

Plants of the new *Clethra* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Caleb'. These characteristics in combination distinguish 'Caleb' as a new and distinct cultivar of *Clethra:*

1. Upright and somewhat outwardly spreading plant habit.
2. Vigorous growth habit.
3. Freely branching habit.
4. Dark-green leaves.

5. Large inflorescences with numerous large flowers.
6. Good garden performance.

Plants of the new *Clethra* can be compared to plants of the female parent, 'Ruby Spice'. Plants of the new *Clethra* differ from plants of 'Ruby Spice' in the following characteristics:

1. Plants of the new *Clethra* have larger inflorescences than plants of 'Ruby Spice'.
2. Plants of the new *Clethra* have larger flowers than plants of 'Ruby Spice'.
3. Plants of the new *Clethra* have white-colored flowers whereas plants of 'Ruby Spice' have pink-colored flowers.

Plants of the new *Clethra* can be compared to plants of the *Clethra alnifolia* 'Hummingbird', not patented. In side-by-side comparisons conducted in Grand Haven, Mich., plants of the new *Clethra* differed from plants of 'Hummingbird' in the following characteristics:

1. Plants of the new *Clethra* were larger than plants of 'Hummingbird'.
2. Plants of the new *Clethra* have larger inflorescences than plants of 'Hummingbird'.
3. Plants of the new *Clethra* have larger flowers than plants of 'Hummingbird'.

BRIEF DESCRIPTION OF THE PHOTOGRAPHS

The accompanying colored photographs illustrate the overall appearance of the new *Clethra* plant, showing the colors as true as it is reasonably possible to obtain in colored reproductions of this type. Colors in the photographs may differ slightly from the color values cited in the detailed botanical description which accurately describe the colors of the new *Clethra* plant.

The photograph on the first sheet is a side perspective view of a typical plant of 'Caleb' grown in a container.

The photograph on the second sheet is a close-up view of a typical inflorescence of 'Caleb'.

DETAILED BOTANICAL DESCRIPTION

The aforementioned photographs and following observations, measurements and values describe plants grown in one-gallon containers in Grand Haven, Mich. during the spring and early summer in an outdoor nursery and under conditions which closely approximate commercial production. Plants were two years old when the photographs and the description were taken. In the description, color references are made to The Royal Horticultural Society Colour Chart, 1995 Edition, except where general terms of ordinary dictionary significance are used.

Botanical classification: *Clethra alnifolia* 'Caleb'.

Parentage:

*Female, or seed, parent.*—*Clethra alnifolia* 'Ruby Spice', not patented.

*Male, or pollen, parent.*—Unknown selection of *Clethra alnifolia*, not patented.

Propagation:

*Type.*—By softwood cuttings.

*Time to initiate roots.*—About 30 days at 24° C.

*Time to produce a rooted young plant.*—About four months at 24° C.

*Root description.*—Fine to thick, fibrous; cream to brown in color.

*Rooting habit.*—Freely branching; dense.

Plant description:

*Plant form and growth habit.*—Perennial shrub; upright and somewhat outwardly spreading plant habit; vigorous growth habit.

*Branching habit.*—Freely branching habit with about eight primary lateral branches; pinching (removal of terminal apices) will enhance lateral branch development.

*Plant height.*—About 60 cm.

*Plant diameter* (*area of spread*).—About 40 cm.

Lateral branch description:

*Length.*—About 18 cm.

*Diameter.*—About 5 mm.

*Internode length.*—About 3 cm.

*Texture.*—Smooth, glabrous.

*Color.*—Close to 199A.

Foliage description:

*Arrangement.*—Alternate, simple.

*Length.*—About 7 cm.

*Width.*—About 3.2 mm.

*Shape.*—Ovate.

*Apex.*—Acute.

*Base.*—Cuneate.

*Margin.*—Doubly serrate.

*Texture, upper and lower surfaces.*—Smooth, glabrous.

*Venation pattern.*—Pinnate.

*Color.*—Developing leaves, upper and lower surfaces: Close to 144A. Fully expanded leaves, upper surface: Close to 147A; venation, close to 144B. Fully expanded leaves, lower surface: Close to 147B; venation, close to 144B.

*Petiole.*—Length: About 1 cm. Diameter: About 1 mm. Texture, upper and lower surfaces: Smooth, glabrous. Color, upper and lower surfaces: Close to 139D.

Flower description:

*Flower appearance/arrangement.*—Relatively large single rotate flowers arranged in terminal panicles; freely flowering habit with usually about 60 flowers per inflorescence; flowers face mostly upright to outwardly.

*Flower longevity.*—Flowers last for about four to five weeks on the plant; flowers not persistent.

*Natural flowering season.*—Continuous flowering during the summer in Grand Haven, Mich.

*Fragrance.*—Fragrant; sweet, pleasant.

*Inflorescence height.*—About 20 cm.

*Inflorescence diameter.*—About 4 cm.

*Flower diameter.*—About 2 cm.

*Flower length* (*height*).—About 1.5 cm.

*Flower bud.*—Length: About 5 mm. Diameter: About 3 mm. Shape: Ovoid. Color: Close to 145B.

*Petals.*—Quantity per flower: Single whorl of five. Length: About 1 cm. Width: About 4 mm. Shape: Oblong. Apex: Retuse. Margin: Entire. Texture, upper and lower surfaces: Smooth, glabrous. Color: When opening, upper and lower surfaces: Close to 150D. Fully opened, upper and lower surfaces: Close to 155D.

*Sepals.*—Quantity per flower: Single whorl of five. Length: About 5 mm. Width: About 3 mm. Shape: Rounded. Apex: Acute. Margin: Entire. Texture, upper and lower surfaces: Smooth, glabrous. Color: When opening, upper and lower surfaces: Close to 145A. Fully opened, upper and lower surfaces: Close to 145B.

*Pedicels.*—Length: About 6 mm to 9 mm. Diameter: About 3 mm. Strength: Strong. Texture: Smooth, glabrous. Color: Close to 145B.

*Reproductive organs.*—Androecium: Anther shape: Oblong. Anther length: About 2 mm. Anther color: Close to 145C. Amount of pollen: Scarce. Pollen color: Close to 163A. Gynoecium: Pistil length: About 5 mm. Style length: About 4 mm. Style color: Close to 145C. Stigma appearance: Rounded. Stigma color: Close to 145C. Ovary color: Close to 141C.

*Seeds.*—Length: About 4 mm. Diameter: About 4 mm. Color: Close to 145C.

Garden performance: Plants of the new *Clethra* have been observed to have good garden performance and to tolerate rain, wind and temperatures ranging from about −27° C. to about 37° C.

Pathogen/pest resistance: Plants of the new *Clethra* have not been observed to be resistant to pathogens and pests common to *Clethra*.

It is claimed:

1. A new and distinct *Clethra* plant named 'Caleb' as illustrated and described.

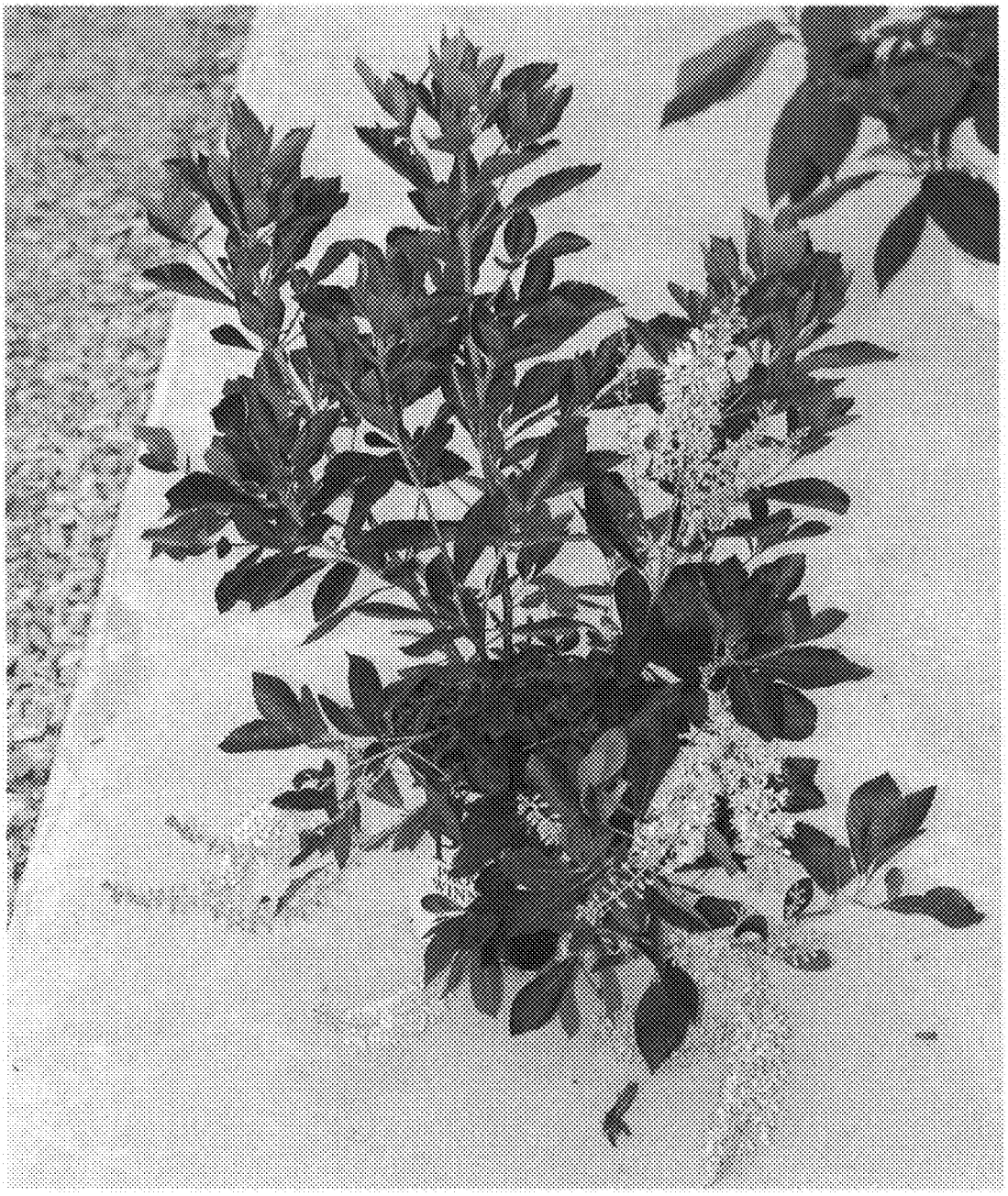

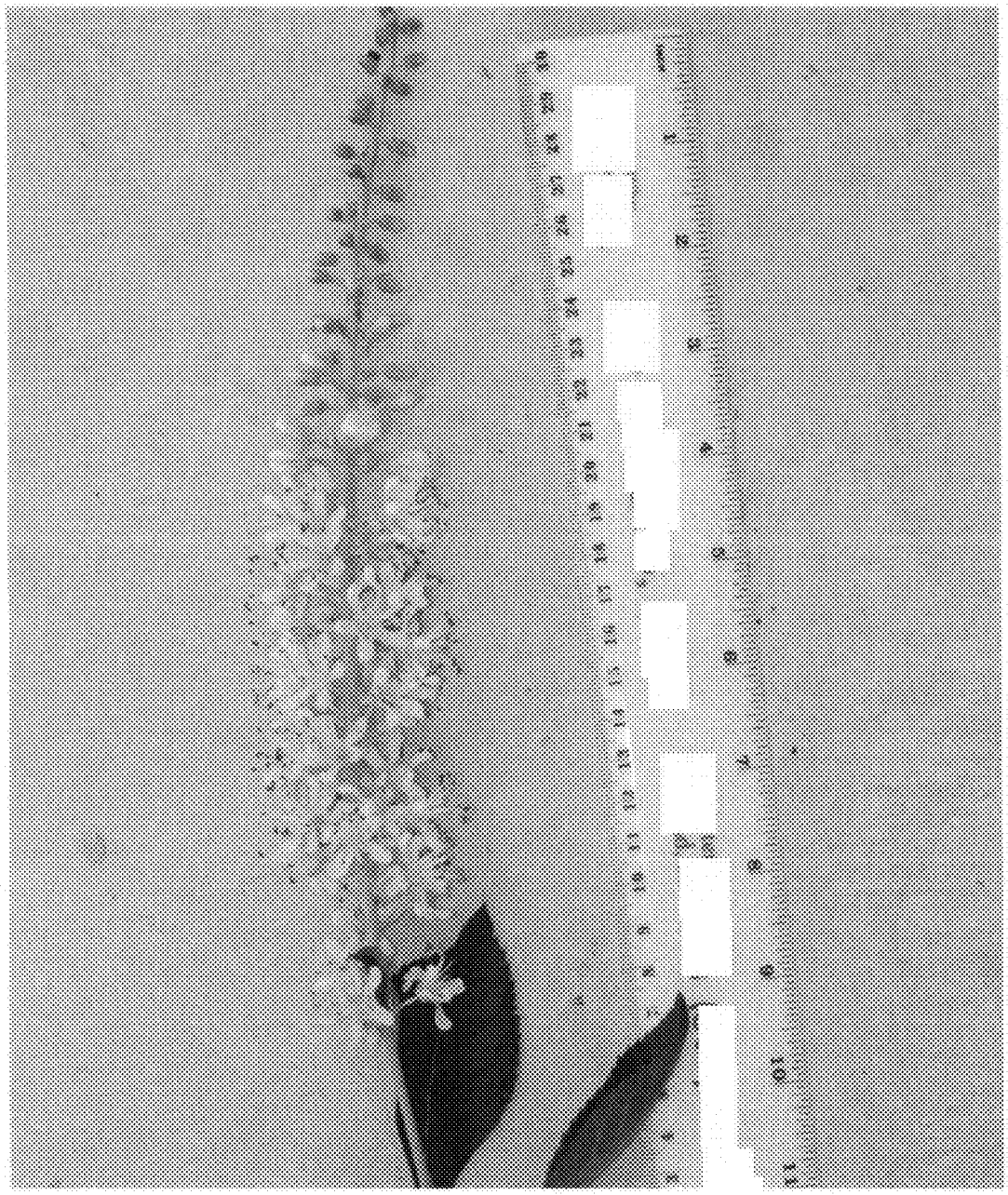

* * * * *